US006239104B1

(12) United States Patent
Pettit et al.

(10) Patent No.: US 6,239,104 B1
(45) Date of Patent: May 29, 2001

(54) ISOLATION AND STRUCTURAL ELUCIDATION OF THE CYTOSTATIC LINEAR AND CYCLO-DEPSIPEPTIDES DOLASTATIN 16, DOLASTATIN 17, AND DOLASTATIN 18

(75) Inventors: George R. Pettit, Paradise Valley; Jun-ping Xu, Chandler, both of AZ (US)

(73) Assignee: Arizona Board of Regents, Tempe, AZ (US)

(*) Notice: Subject to any disclaimer, the term of this patent is extended or adjusted under 35 U.S.C. 154(b) by 0 days.

(21) Appl. No.: 09/380,016

(22) PCT Filed: Feb. 23, 1998

(86) PCT No.: PCT/US98/03455

§ 371 Date: Dec. 1, 1999

§ 102(e) Date: Dec. 1, 1999

(87) PCT Pub. No.: WO98/36765

PCT Pub. Date: Aug. 27, 1998

Related U.S. Application Data

(60) Provisional application No. 60/044,426, filed on Feb. 25, 1997.

(51) Int. Cl.⁷ .................................................. A61K 38/00
(52) U.S. Cl. .................................. 514/9; 424/520; 514/9; 514/16; 514/17; 514/19; 530/323; 530/329; 530/330; 530/333; 548/204

(58) Field of Search .................. 424/520; 514/9, 514/16, 17, 19; 530/323, 329, 330, 333; 548/204

(56) References Cited

U.S. PATENT DOCUMENTS

| 5,410,024 | 4/1995 | Pettit et al. | 530/330 |
| 5,504,191 | 4/1996 | Pettit et al. | 530/330 |
| 5,521,284 | 5/1996 | Pettit et al. | 530/330 |
| 5,530,097 | 6/1996 | Pettit et al. | 530/330 |
| 5,554,725 | 9/1996 | Pettit | 530/330 |
| 5,599,902 | 2/1997 | Pettit et al. | 530/330 |
| 5,635,483 | 6/1997 | Pettit et al. | 514/17 |
| 5,663,149 | 9/1997 | Pettit et al. | 514/17 |
| 5,665,860 | 9/1997 | Pettit et al. | 530/330 |

Primary Examiner—Christopher S. F. Low
Assistant Examiner—Stephen Tu
(74) Attorney, Agent, or Firm—Richard R. Mybeck

(57) ABSTRACT

Cytostatic linear and cyclo-depsipeptides, "Dolastatin 16", "Dolastatin 18", and "Dolastatin 17", are disclosed which are obtained from Indian Ocean shelless mollusk *Dolabella auricularia*. Methods of using the substances to inhibit malignant cell growth associated with neoplastic diseases in animals and humans are also disclosed, as well as pharmaceutical preparations containing Dolastatin 16, Dolastatin 17, and Dolastatin 18.

10 Claims, 1 Drawing Sheet

ISOLATION AND STRUCTURAL ELUCIDATION OF THE CYTOSTATIC LINEAR AND CYCLO-DEPSIPEPTIDES DOLASTATIN 16, DOLASTATIN 17, AND DOLASTATIN 18

The present application claims priority rights based on U.S. Provisional Application Ser. No. 60/044,426 filed Feb. 25, 1997.

GOVERNMENT LICENSING RIGHTS

Financial assistance was provided by the National Science Foundation Grants BBS 88-04992, CHE-8409644 and CHE-8620177 and numerous private foundations. This invention was made with Government support and the Government has certain rights in the invention.

INTRODUCTION

The present invention relates to cytostatic linear and cyclo-depsipeptides herein denominated "Dolastatin 16," "Dolastatin 17," and "Dolastatin 18" which are obtained from the Indian Ocean shell-less mollusk *Dolabella auricularia;* and to methods of using such substances to inhibit malignant cell growth associated with neoplastic diseases in animals and humans afflicted therewith, including pharmaceutical preparations containing Dolastatin 16, Dolastatin 17 and Dolastatin 18 and their derivatives.

BACKGROUND OF THE INVENTION

The great Roman natural scientist Gaius Plinius Secundus (Pliny the Elder) first described Indian Ocean sea hare of the genus Dolabella around 60 A.D. (The Romans first designated Mollusca of the family Aplysidae as sea hares because of the similarity between the ears of a hare and the auriculate tentacles of these gastropods). However, a consideration of the potential of the Indian Ocean Dolabella with respect to modern medical problems is only of recent origin. For example, see the following patents which are hereby incorporated by reference: U.S. Pat. No. 4,414,205, Nov. 8, 1983, Dolastatins 1-3; U.S. Pat. No. 4,486,414, Dec. 4, 1984, Dolastatins A and B; U.S. Pat. No. 4,816,444, Mar. 28, 1989, Dolastatin 10; U.S. Pat. No. 4,879,278, Nov. 7, 1989, Dolastatin 15; U.S. Pat. No. 4,986,988, Jun. 22, 1991, Dolastatin 13 and Dehydrodolastatin 13; and U.S. Pat. No. 5,138,036, Aug. 11, 1992, Dolastatin 14. The aforementioned Dolastatins may correspond to *D. auricularia* constituents (See: 1969 Ph.D. dissertation of M. Watson. U. of Hawaii, "Some Aspects of the Pharmacology, Chemistry and Biology of the Midgut Gland Toxins of Some Hawaiian Sea Hares, especially *Dolabella auricularia* and *Aplysia pulmonica*", University Microfilms Inc., Ann Arbor, Mich.)

The biological properties exhibited by the *Dolabella auricularia* have been pursued for centuries, but it was only in 1972 that this laboratory found Indian Ocean specimens of this sea hare which yielded extracts that proved effective (over 100% increase in life span) against the U.S. National Cancer Institute's (NCI) murine P388 lymphocytic leukemia (PS system). Subsequently, the Cancer Research Institute at Arizona State University, Tempe, Ariz., succeeded in isolating many new (and powerful) cell growth inhibitory and/or antineoplastic peptides from *Dolabella auricularia* by using solvent separation techniques to fractionate these peptides in combination with bioassaying the fractionated aliquots for antineoplastic activity. Because the sea hare yields only very small quantities of antineoplastic substances (about 1 mg each from 100 kg), isolating and elucidating the structure of these peptides is exceptionally challenging.

Of the early work, Dolastatin 1 was found to be the most active (lowest dose) antineoplastic substance (33% cure rate against the NCI murine B16 melanoma at 11 pg/kg) known in its time. Later another substance was isolated and determined to be a unique linear pentapeptide and was denominated "Dolastatin 10". *Dolabella auricularia* antineoplastic constituent appeared to be the most active (lowest dose) antineoplastic substance found up to its time. In practice, Dolastatin 10 showed a 17–67% curative response at 3.25–26 $\mu$g/kg against the National Cancer Institute ("NCI") human melanoma xenograph (nude mouse), 42–138% life extension at 1.44–11.1 $\mu$g/kg using the B16 melanoma and 69–102% life extension at 1–4 $\mu$g/kg against the PS leukemia ($ED_{50}$ =4.6×10$^5$ $\mu$g/ml). In contrast, Dolastatin 14 is strongly active against NCI's P388 lymphocytic leukemia (PS System) (See: Schmidt et al, *Experienta,* 1978, 37, 659–660) cell line with $ED_{50}$ of 0.0018 $\mu$g/ml. The PS System is generally accepted as an excellent predictor of activity against various types of human cancer (See: Vendetti et al, *Lloydia,* 30,332 et seq. (1967) and references cited therein).

SUMMARY OF THE INVENTION

The present invention relates to the discovery of new and potent cytostatic substances denominated Dolastatin 16, Dolastatin 17, and Dolastatin 18 which are extracted from the Indian Ocean shell-less mollusk *Dolabella auricularia* in the manner hereinafter described in detail. The substances and their pharmaceutically acceptable derivatives can be formulated into useful pharmaceutical preparations having demonstrable and confirmable levels of cell growth inhibitory activity when measured by the generally accepted protocols in use at the United States National Cancer Institute.

Accordingly, this invention provides a number of new agents useful in the retardation or remission of one or more types of malignant cells.

The present invention also provides methods and procedures for isolating a cell growth inhibitory substance from marine life in a form in which it may be readily and usefully employed in the therapeutic treatment and management of one or more types of neoplasms which occur in human or animal hosts.

Further, the present invention also provides the means and methods of creating useful pharmaceutical preparations for the treatment and management of neoplastic disease which preparations contain as their essential active ingredient a unique cytostatic factor obtained from the Indian Ocean shell-less mollusk *Dolabella auricularia,* its synthetic counterpart, or a pharmaceutically active derivative thereof.

These and still further objects as shall hereinafter appear are readily fulfilled by the present invention as will be readily discerned from the following detailed description of an exemplary embodiment thereof.

BRIEF DESCRIPTION OF THE DRAWING

The invention will be more readily understood from the description of a preferred embodiment that follows and from the diagrammatic FIGURE in the drawing.

In the drawing.

DETAILED DESCRIPTION OF THE INVENTION

The Organism

Figure 1:
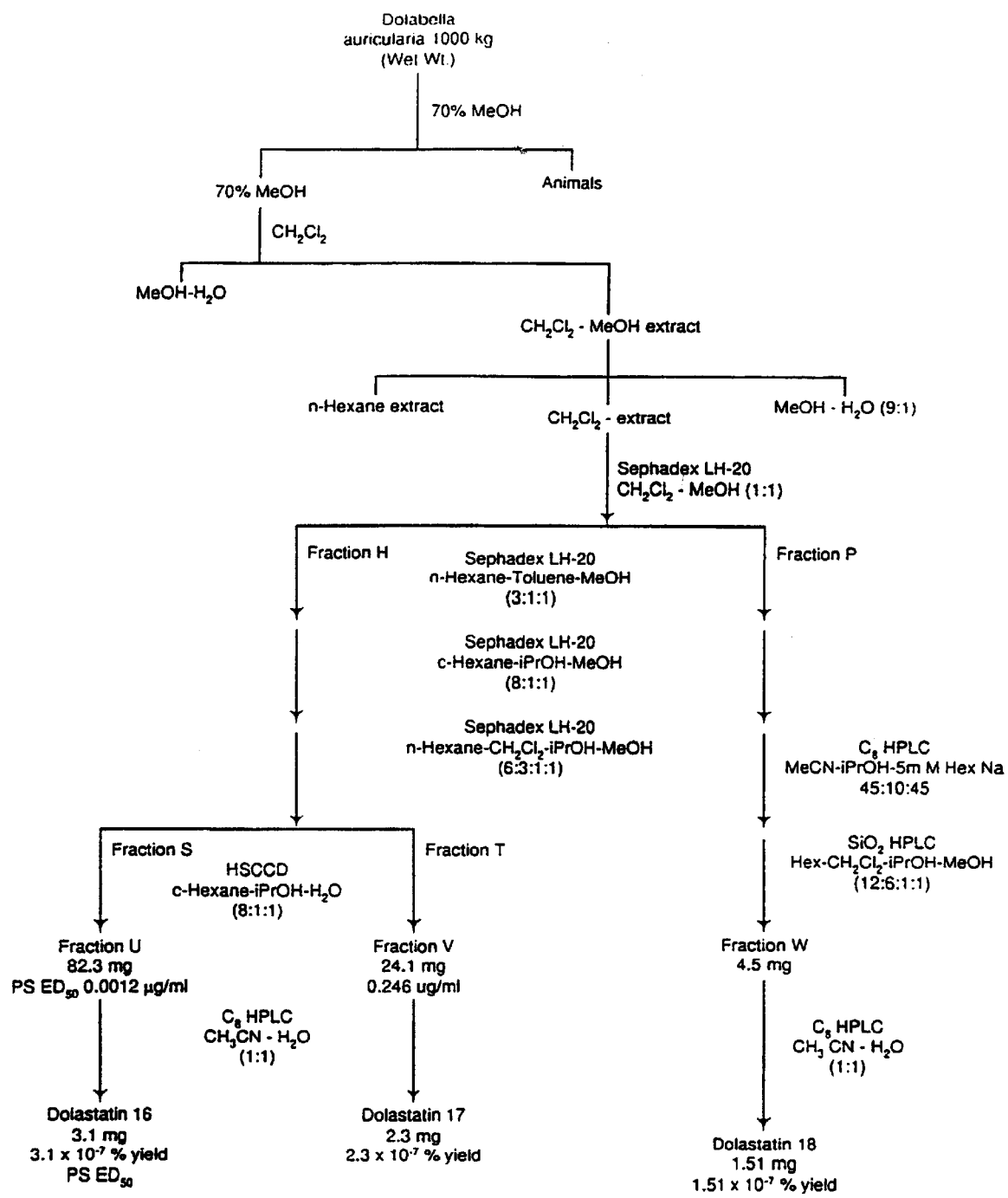
FIG. 1 is a schematic representation of an embodiment of a separation process for isolating Dolastatin 16, Dolastatin 17 and Dolastatin 18.

Taxonomy: *Dolabella auricularia* belongs to the family Aplysidae, the class Gastropoda and the phylum Mollusca.

In a reference by H. Engel in "Zoologische Mededeelingen," Leiden, 24, 197–239 (1945), there are numerous color plates of specimens of Dolabella. Also in this reference is a listing of previously presumed different species of Dolabella which were later found to be the same and identified as *Dolabella auricularia*. These species are: *Dolabella agassizi, D. andersonii, D. hasseltii, D. hemprichii, D. neira, D. peronii, D. rumphii, D. teremidi, D. tongana, D. truncata, D. variegata,* and *D. scapula.*

In appearance, the Dolabella used herein were olive green in color having a pear-shaped body and average length, 15–20 cm. The reference by H. Engel has detailed descriptions of Dolabella collected around the world.

Animal Collection: The Western Indian Ocean (Mauritius) sea hare *Dolabella auricularia* was initially collected in October 1972. The Dolabella collection site used for initial isolation of the Dolastatins was on the eastern side of Mauritius in the Indian Ocean, approximate location, 21 S latitude, 56 E longitude, in 4–5 ft. deep water off the coast of the island.

Another site where Dolabella can be collected is near Negros Island in the Philippines, approximate location 9 N latitude, 123 E longitude. By March 1975, confirmed activity of an ethanol extract against the National Cancer Institute's (NCI) P388 lymphocyte leukemia (PS system) was established and showed T/C 235 at 600 mg to 167 at 176 mg/kg. Extracts of Dolabella species from five separate collections all demonstrated antineoplastic activity.

A series of analogous extracts from subsequent collections of the sea hare gave comparable results. The results reported herein were conducted with a 1983 collection preserved in ethanol. The total volume of animal (~1000 kg) and ethanol was 700 gallons.

Isolation and Purification of Dolastatin 16,
Dolastatin 17 and Dolastatin 18

A variety of methods can be used to isolate and purify the various Dolastatins from samples of sea hare, such as, solvent extraction, partition chromatography, silica gel chromatography, liquid-liquid distribution in a Craig or Ito apparatus, adsorption on resins, and crystallization from solvents.

A. Isolation of Dolastatin 16 Dolastatin 17 and Dolastatin 18

A combined ethanol-2-propanol extract of *D. auricularia* (1000 kg. wet, collected in 1983) was concentrated to an active methylene chloride fraction by a series of solvent partition steps. The steps for extracting the active methylene chloride fraction have been described in U.S. Pat. Nos. 4,414,205, 4,486,414, 4,816,444, 4,879,278, 4,986,988, and 5,138,036 as previously incorporated by reference. Subsequent fractionation of the active methylene fraction is accomplished by extensive column chromatographic separation (stearic exclusion and gel permeation on SEPHADEX®, partition and adsorption on silica gel, and high pressure liquid chromatography, "HPLC") using gradient elution techniques guided by PS bioassaying. Solvents used for column chromatography were freshly distilled. The SEPHADEX LH-20, particle size 25–100 μm, used in the gel permeation and partition column chromatographic separations was obtained from Pharmacia Fine Chemicals AB, Uppsala, Sweden. GILSON FC-220 race track and FC-80 microfractionators connected to GILSON HM UV-VISIBLE HOLOCHROME detectors were used for chromatographic fractionation experiments. Column chromatographic procedures with silica gel utilized the 70–230 mesh of SILICA GEL 60 prepacked columns supplied by E. Merck (Darmstadt). A PARTISIL M9 10/50 ODS-2 (C-18 reverse phase) column (9.4 mm i.d. by 500 mm) was used for HPLC and obtained from Whatman, Inc., Clifton, N.J. Preparative layer plates were obtained from Whatman, Inc. and the SILICA GEL GF Uniplates for thin layer chromatography (hereinafter "TLC") were supplied by Analtech, Inc., Newark, Del. The TLC plates were viewed with UV light, developed with an anisaldehyde-acetic acid-sulfuric acid spray (heating to approximately 150° C. for 10 minutes) or with ceric sulfate-sulfuric acid (heating for 10 minutes).

In one embodiment of the present invention, the active methylene chloride fraction can be initially separated by single solvent partition using a one to one mixture of methylene chloride and methanol over SEPHADEX LH-20. This results in the formation of two active fractions, fraction H and fraction P.

These fractions H and P are subsequently separated using a series of solvent partitions including gel permeation (SEPHADEX LH-20) and partition (LH-20) column chromatography interspersed by high-speed countercurrent distribution procedures. This results in the intermediate fractions S and T. and final fractions U, V, and W. Final separation and purification was accomplished by reverse phase C8 HPLC with acetonitrile-water, in a one to one ratio, as a mobile phase to afford Dolastatin 16 as a colorless amorphous powder: 3.1 mg total ($3.1 \times 10^{-7}$ yield) and $(\alpha)_D^{20} +15.5°$ (c=0.20, $CH_3OH$); Dolastatin 17 as a colorless amorphous powder: 2.3 mg total ($2.3 \times 10^{-7}$ yield) and $(\alpha)_D^{20} +145°$ (c=0.14, $CH_3OH$), and Dolastatin 18 as a colorless amorphous powder: 1.51 mg total ($1.51 \times 10^{-7}$ yield) from the final fractions U, V, and W, respectively. A representation of the separation process steps is shown in FIG. 1.

B. Structural Determination of Dolastatin 16,
Dolastatin 17, and Dolastatin 18

1. General Methods of Characterization

Amino acid analysis were performed with a BECKMAN Model 121 unit. Ultraviolet spectra were recorded using a HEWLETT-PACKARD 8450A UV/VIS spectrophotometer equipped with a HP7225A plotter. Optical rotations were measured on a PERKIN-ELMER model 241 polarimeter using a sodium lamp operating at 589 nm through a 10 cm microcell. Infrared spectra (IR) were recorded on a NICOLET FTIR model MX-1 spectrometer. High resolution fast atom bombardment mass spectra (HRFAB-MS) were recorded in a 3-NBA-matrix in the positive ion mode on a KRATOS MS-50 spectrometer. All one dimensional (1D) and two dimensional (2D) $^1H$ and $^{13}C$ NMR experiments were performed at ambient temperature on a VARIAN VXR 500s NMR (using various solvents) instrument equipped with a SUN MICROSYSTEM computer.

Two dimensional homonuclear proton chemical shift correlation experiments were measured by employing a conventional pulse sequence. The TOCSY experiment was carried out in the phase sensitive mode (TPP1) using a MLEV 17 (mixing time 80 ms) and three Pro units and one each of lactic acid (Lac) and 2-hydroxyisovaleric acid (Hiv). In addition to these units, two new amino acid components were identified as 2-amino-4-phenylisovaleric acid and 2-methyl-3-aminoisocaproic acid, designated dolaphenvaline (Dpv) and dolamethylleuine (Dml) respectively. Both were also confirmed by HMBC correlations as shown in table 1.

TABLE 1

The $^1$H- and $^{13}$C- NMR Spectral Data Assignments of Dolastatin 16 (in CDCl$_3$)

| No. | $^{13}$C ppm | $^1$H ppm | J (Hz) | HMBC ($^1$H to $^{13}$C) |
|---|---|---|---|---|
| Pro$^1$CO | 174.24 s | | | |
| α | 61.28 d | 43.62 dd | (7.2, 2.0) | CO, β, γ, δ |
| β | 30.70 t | 2.18 m | | |
| | | 2.26 m | | CO, α, γ |
| γ | 24.78 t | 1.99 m | | |
| | | 2.08 m | | β |
| δ | 47.55 t | 3.45 m | | γ |
| | | 3.91 m | | α, β, γ |
| Dpv$^2$CO | 171.31 s | | | |
| α | 50.59 d | 4.95 d | (7.2) | Pro$^1$CO, CO, β, γ, γ' |
| β | 40.90 d | 1.75 m | | γ |
| γ | 40.95 d | 2.39 m | | α, β, γ, 1, 2/6 |
| | | 2.52 d | (7.6) | α, β, γ, 1, 2/6 |
| γ' | 15.13 q | 0.80 d | (5.2) | α, β, γ |
| 1 | 140.60 s | | | |
| 2/6 | 129.56 d | 7.35 d | (6.0) | γ, 4 |
| 3/4 | 128.33 d | 7.27 d | (6.0) | 1 |
| 5 | 125.15 d | 7.17 dd | (6.0, 6.0) | 2/6 |
| NH | | 6.73 d | (7.2) | Pro$^1$CO, CO |
| Pro$^3$CO | 171.01 s | | | |
| α | 58.84 d | 4.55 d | (6.0) | CO, β, γ, δ |
| β | 25.49 t | 1.51 m | | CO |
| | | 2.40 m | | CO, γ, δ |
| γ | 25.01 t | 1.73 m | | α |
| | | 1.84 m | | |
| δ | 45.89 t | 2.52 m | | β |
| | | 2.83 m | | γ |
| Dml$^4$CO | 174.64 s | | | |
| α | 38.67 d | 2.85 m | | CO, β' |
| β | 56.35 d | 3.66 m | | Pro$^3$CO, CO, α, γ |
| β' | 14.89 q | 1.01 d | (5.6) | CO, α, β |
| γ | 32.31 d | 1.53 m | | |
| δ | 19.73 q | 0.87 d | (5.6) | β, γ, δ' |
| δ' | 20.29 q | 0.88 d | (5.6) | β, γ, δ |
| NH | | 7.68 d | (8.0) | Pro$^3$CO |
| Lac$^5$CO | 169.02 s | | | |
| α | 66.64 d | 5.18 q | (7.0) | Dml$^4$CO, CO, β |
| β | 17.20 q | 1.44 d | (7.0) | CO, α |
| Pro$^6$CO | 171.01 s | | | |
| α | 57.82 d | 4.45 d | (6.4) | CO, β, γ, δ |
| β | 30.82 t | 2.20 m | | CO |
| | | 2.30 m | | CO, δ |
| γ | 21.77 t | 1.95 m | | |
| | | 2.07 m | | β |
| δ | 46.43 t | 3.42 m | | γ |
| | | 3.67 m | | |
| Hiv$^7$CO | 169.57 s | | | |
| α | 76.37 d | 5.42 d | (2.8) | Pro$^6$CO, CO, β, γ, γ' |
| β | 28.29 d | 2.18 m | | γ, γ' |
| γ | 16.08 q | 1.04 d | (7.0) | α, β, γ' |
| γ' | 19.73 q | 1.06 d | (7.2) | α, β, γ |
| MeVal$^8$ | | | | |
| CO | 169.30 s | | | |
| α | 59.46 d | 5.16 | (8.8) | CO, β, γ, γ', CH$_3$N |
| β | 25.63 d | 2.36 m | | α, γ, γ' |
| γ | 19.73 q | 0.91 d | (5.6) | α, β, γ' |
| γ' | 17.75 q | 0.83 d | (5.2) | α, β, γ |
| CH$_3$N | 29.26 q | 3.09 s | | Hiv$^7$CO, CO |

The bonding sequence of the depsipeptide units was determined by interpretation of the HMBC, NOESY and ROESY spectra and confirmed in major part by results of high-resolution MS/MS tandem mass spectral studies. The HMBC correlations from NH[Dpv$^2$] to CO [Pro$^1$] indicated the presence of the Pro$^1$—Dpv$^2$ segment A (some HMBC ($\frown$) correlations):

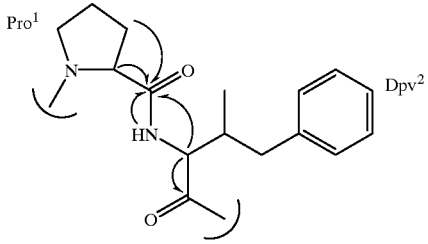

Two HMBC cross peaks observed between CH$_3$N [MeVal$^8$]/CO[Hiv$^7$] and αH[Hiv$^7$]/CO[Pro$^6$] confirmed the connections in segment B as Pro$^6$—O—Hiv$^7$—MeVal$^8$ (some HMBC ($\frown$) correlations):

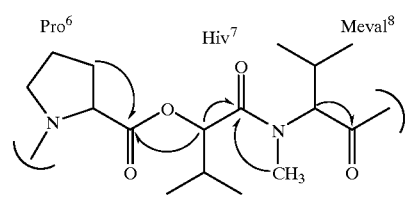

Another three HMBC correlation sets corresponding to αH[Lac$^5$]/CO[Dml$^4$], αH[Dml$^4$]/CO[Pro$^3$], and NH[Dml$^4$]/CO[Pro$^3$] allowed the structure of segment C to be assigned Pro$^3$—Dml$^4$—O—Lac$^5$ (some HMBC ($\frown$) correlations):

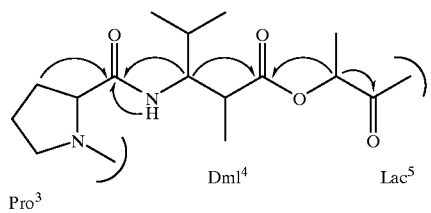

Because the unsaturation number calculated from the molecular formula suggested that Dolastatin 16 was a cyclic octadepsipeptide, the correct sequence of segments A, B, and C would be one of two possibilities, either cyclo-[A-B-C] or cyclo-[A-C-B]. Considerable evidence in support of the overall structure was provided by results of tandem MS/MS analyses.

Further interpretation of both the NOESY and ROESY spectra afforded the most important evidence used to assign the sequence. The nOe relationships found between αH[MeVal$^8$]/δH$_2$[Pro$^1$], αH[Lac$^5$]/αH[Pro$^6$], βH$_3$[Lac$^5$]/αH[Pro$^6$], and δH$_2$[Pro$^3$]/αH[Dpv$^2$], as well as NH[Dml$^4$]/αH[Pro$^3$] and the N—CH$_3$ of [MeVal$^8$]/αH[Hiv$^7$], finally confirmed the correct segment sequence to be cyclo-[A-C-B]. The assignment was also in agreement with other HMBC and nOe cross peak correlations. Therefore, the overall structure of Dolastatin 16 was established as cyclo-(Pro$^1$—Dpv$^2$—Pro$^3$—Dml$^4$—O—Lac$^5$—Pro$^6$—O—Hiv$^7$—MeVal$^8$).

The strong nOe relationship with αH[Lac$^5$] to αH[Pro$^6$] suggested a cis orientation for the Lac$^5$—Pro$^6$ amide bond. That observation was further supported by the difference in chemical shifts of the β and γ carbons ($\Delta\delta_{\beta\gamma}$=9.05 ppm) of the Pro$^6$ residue. The two Pro amide bonds involving MeVal[8]—Pro[1] and Dpv[2]—Pro[3] appeared to be trans, as $\Delta\delta_{\beta\eta}$ for both Pro units was 6 ppm.

The absolute stereochemistry of the unit components other than Dpv[2] and Dml[4] was determined by chiral HPLC analyses of the Dolastatin 16 using 6N hydrochloric acid hydrolysate. Conditions for the chiral HPLC analysis included: a 4.6 by 50 mm column containing CHIREX phase 3126 (Phenomenex); two chromatographic solvents: either a 2 mM $CuSO_4$ aqueous solution for α-amino acids and lactic acid, or a 2 mM $H_2O$—$CH_3CN$:$CuSO_4$ (9:1) solution for 2-hydroxyvaleric acid; and a UV-VIS detection device set at 230.4 nm and 500 nm. The configurations of Lac[5] and the three Pro units were established to be all L (S), while the MeVal[8] and Hiv[7] units were found to have the D(R)-configuration by comparing those observed in Dolastatin 16 to reference L and D α-amino acids. Thus, the structure elucidated for Dolastatin 16 is (HMBC (⌒) and nOe (⌒) correlations):

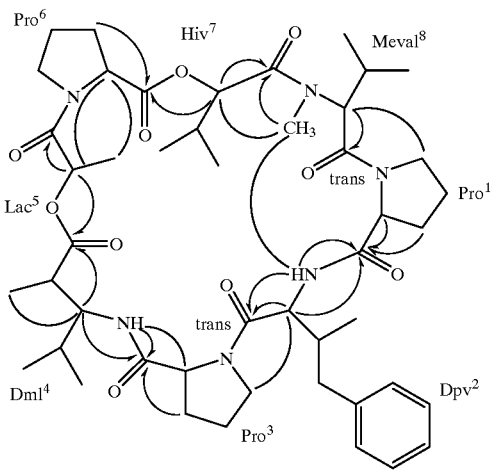

Assignment of the remaining chiral centers will require a series of synthetic approaches where the overall objective will be a convenient total synthesis. That research is under way and will eventually allow a more detailed assessment of the promising antineoplastic activity.

The administration of Dolastatin 16 is useful for treating neoplastic disease associated with malignant cell growth, and expectedly its synthetic counterpart, as well as, its pharmaceutically and physiologically active derivatives will be useful for treating neoplastic disease associated with malignant cell growth in animals and humans. For example, Dolastatin 16 was screened against a minipanel of the U.S. National Cancer Institute's human cancer cell lines utilizing protocols described by Michael R. Boyd and Kenneth D. Paul in *Some Practical Considerations and Applications of the National Cancer Institute In Vitro Anticancer Drug Discovery Screen,* 34 DRUG DEVELOPMENT RESEARCH 91 (1995) (and references cited therein). Dolastatin 16 strongly inhibited the growth of the lung (NCI-H460, $GI_{50}$ 0.00096 μg/mL, colon (KM 20L2, $GI_{50}$ 0.0012 μg/mL, brain (SF-295, $GI_{50}$ 0.0052 μg/mL) and melanoma (SK-MEL-5, $GI_{50}$ 0.0033 μg/mL) specimens. Dolastatin 16 showed mean panel $GI_{50}$ values of $2.5 \times 10^{-7}$ M using the complete panel of sixty human cancer cell lines and relatively low $GI_{50}$-COMPARE correlations of 0.76 and 0.71 with Dolastatins 10 and 15, respectively. Importantly, against breast cancer lines MCF7, MDA-MB-435 and MDA-N, the $GI_{50}$ values ($log_{10}$) in that order were found to be −7.32, −7.46 and −7.54 M. Dolastatin 16 gave comparable inhibitory results using five human leukemia cell lines.

It is expected that unit dosage forms of Dolastatin 16 could be prepared according to selected compositions described in the examples incorporated by reference from U.S. Pat. Nos. 4,414,205, 4,486,414, 4,816,444, 4,879,278, 4,986,988, and 5,138,036 except that Dolastatin 16 would be substituted as the active ingredient (e.g. substitute Dolastatin 16 for Dolastatin 14 in U.S. Pat. No. 5,138,036). Illustratively, expected dosage levels of the administered active ingredients would be: subcutaneously, 1 to about 50 mg/kg; intravenous, 0.4 to about 20 mg/kg; intramuscular, 1 to about 50 mg/kg; orally, 5 to 100 mg/kg; intranasal instillation, 5 to about 100 mg/kg; and aerosol, 5 to 100 mg/kg. As used herein, mg/kg means weight of active ingredients in milligrams divided by the body weight of the host in kilograms. The dose administered will be dependent upon the identity of the neoplastic disease; the type of host involved, including its age, health and weight; the kind of concurrent treatment employed, if any; and the frequency of treatment and therapeutic ratio.

From the foregoing, it becomes readily apparent new and useful antineoplastic preparations have been herein described and illustrated which fulfill all of the aforestated objectives. It is of course understood that such modifications, alterations and adaptations as will readily occur to the artisan confronted with this disclosure are intended within the scope of the invention.

3. Structure and Activity of Dolastatin 17

The HRFAB mass spectrum of the amorphous substance denominated Dolastatin 17 afforded a quasi-molecular ion at m/z 774.500914 $[M+H]^+$ which corresponded to molecular formula $C_{41}H_{67}N_5O_9$. An IR spectrum of Dolastatin 17 contained bands at 3350, 2900, 2116, 1740, 1643, and 1520 $cm^{-1}$ suggesting that Dolastatin 17 contained an alkyne group.

All 1D and 2D-NMR of Dolastatin 17 were measured in two solvents ($CDCl_3$ and DMSO-$d_6$). Analysis of the two series of [1]HO, APT HCOSY, TOCSY and HMQC NMR (500 MHZ) spectra combined with the HMBC, NOESY and ROESY NMR spectral results established the presence of seven independent spin systems: One Pro, one Leu, two MeVal, two 2-hydroxy-isovaleric acid (Hiv) units and a new β-amino acid (hereinafter "Doy") unit including a terminal alkyne group. The partial molecular formula of the new Doy unit was found to be $C_8H_{11}NO$ by HRFAB mass spectral analysis. Interpretation of cross peaks (Table 2) observed in the 2D-NMR spectra led to assignment 3-amino-6-octyneoic acid (Doy) for the new β-amino acid unit. Such β-amino acid having an alkyne group is rarely encountered in marine invertebrates. Interestingly, the mollusc Onchidium sp. collected off New Caledonia has been found to contain the dimeric cyclic-depsipeptide onchidin (2) that contains a methyl derivative of Doy. See Golakoti, G.; et al., 117 J. Amer. Chem. Soc. 12030 (1995).

TABLE 2

The $^1$H- and $^{13}$C- NMR Spectral Data Assignments of Dolastatin 17 (in $CDCl_3$)

| No. | [13]C ppm | $^1$H ppm | J (Hz) | HMBC ($^1$H to $^{13}$C) |
|---|---|---|---|---|
| Pro[1]CO | 171.81 s | | | |
| α | 57.27 d | 5.12 dd | (9.0, 5.0) | CO, β, γ |

TABLE 2-continued

The $^1$H- and $^{13}$C- NMR Spectral Data Assignments of Dolastatin 17 (in CDCl$_3$)

| No. | $^{13}$C ppm | $^1$H ppm | J (Hz) | HMBC ($^1$H to $^{13}$C) |
|---|---|---|---|---|
| β | 29.68 t | 1.80 m | | CO |
| | | 2.38 m | | CO |
| γ | 24.81 t | 2.00 m | | α, β, δ |
| δ | 47.06 t | 3.55 dd | (9, 7.5) | α, β |
| | | 3.91 m | | α, β |
| MeVal$^2$ | | | | |
| CO | 171.27 s | | | |
| α | 64.51 d | 4.23 d | (8.5) | Pro$^1$CO, CO, β, γ, γ', CH$_3$N |
| β | 29.47 d | 2.35 m | | α, γ, γ' |
| γ | 20.43 q | 1.20 d | (6.5) | α, β, γ' |
| γ' | 21.40 q | 1.07 d | (7.0) | α, β, γ |
| CH$_3$N | 30.49 q | 2.92 s | | Pro$^1$CO, CO, α |
| Hiv$^3$CO | 169.54 s | | | |
| α | 76.60 d | 5.21 d | (3.0) | MeVal$^2$CO, CO β, γ, γ' |
| β | 28.92 d | 2.14 m | | γ, γ' |
| γ | 20.07 q | 1.10 d | (7.0) | α, β, γ' |
| γ' | 16.31 q | 0.99 d | (7.0) | α, β, γ |
| MeVal$^4$ | | | | |
| CO | 168.98 s | | | |
| α | 62.15 d | 4.68 d | (10) | Hiv$^3$CO, CO, β, γ, γ' |
| β | 25.58 d | 2.30 m | | α, γ, γ' |
| γ | 17.91 q | 0.78 d | (6.5) | α, β, γ' |
| γ' | 19.83 q | 0.95 d | (7.0) | α, β, γ |
| CH$_3$N | 29.81 q | 2.92 s | | Hiv$^3$CO, CO |
| Lac$^5$CO | 172.08 s | | | |
| α | 51.64 d | 4.60 m | | MeVal$^4$CO, CO, β, γ |
| β | 38.39 t | 1.68 m | | γ, δ, δ' |
| γ | 24.65 d | 1.61 m | | β, δ, δ' |
| δ | 23.59 q | 0.86 q | (7.0) | β, γ, δ' |
| δ' | 20.87 q | 0.84 q | (7.5) | β, γ, δ |
| NH | | 7.25 d | (7.8) | MeVal$^4$CO, α |
| Doy$^6$CO | 170.17 s | | | |
| α | 39.51 t | 2.27 m | | CO, β, γ |
| | | 2.79 dd | (16,6) | CO, β, γ |
| β | 45.32 d | 4.32 m | | |
| γ | 33.99 t | 1.52 m | | α, β, ε |
| | | 1.64 m | | α, β, ε |
| δ | 24.48 t | 1.52 m | | |
| ε | 18.18 t | 2.16 m | | γ, ζ |
| ζ | 68.43 s | | | |
| ξ | 84.20 d | 1.91 s | | ε |
| NH | | 6.10 d | (7.8) | Leu$^5$CO, α, β |
| Hiv$^7$CO | 167.20 s | | | |
| α | 76.17 d | 5.03 d | (3.0) | Doy$^6$CO, CO, β, γ, γ' |
| β | 29.47 d | 2.35 m | | γ, γ' |
| γ | 16.21 q | 0.98 d | (7.0) | α, β, γ' |
| γ' | 20.02 q | 1.02 d | (7.0) | α, β, γ |

The sequence of peptide bonds identified by the HMBC correlations was further confirmed by NOESY and ROESY experiments. An nOe relationship from δ3.69 and δ3.55 to δ5.03 revealed that the carbonyl carbon of Hiv$^2$ was linked through the nitrogen of Pro$^1$. That established Dolastatin 17 as a cyclic depsipeptide. Evidence supporting a cyclic depsipeptide structure was also obtained by considering the molecular formula unsaturation numbers.

The difference in chemical shifts of the β- and γ-carbons of Pro$^1$ (Δδ$_{βγ}$=4.78 ppm) pointed to the presence of a trans-Hiv$^7$—Pro$^1$ conformation. A hydrolysis procedure (6N HCl), and chiral analyses established the Leu, Pro, MeVal and Hiv amino acid hydroxy acid units as all L(S) by using comparing those observed in Dolastatin 17 to reference L and D α-amino acids. Conditions for the chiral HPLC analysis included: a 4.6 by 50 mm column containing CHIREX phase 3126 (Phenomenex); two chromatographic solvents: either a 2 mM CuSO$_4$ aqueous solution for α-amino acids and lactic acid, or a 2 mM H$_2$O—CH$_3$CN:CuSO$_4$, (9:1) solution for 2-hydroxyvaleric acid; and a UV-VIS detection device set at 230.4 nm and 500 nm. Thus, the structure elucidated for Dolastatin 17 is (HMBC (⌒) and nOe (⌒) correlations):

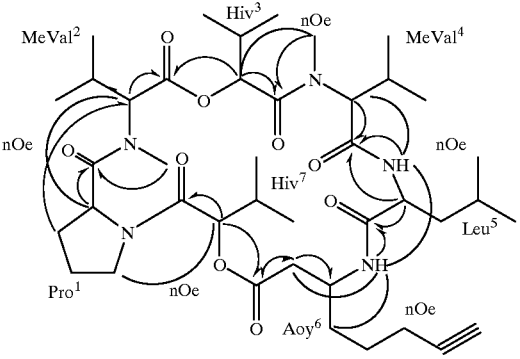

Assignment of the remaining chiral centers will require a series of synthetic approaches where the overall objective will be a convenient total synthesis. Eventual total synthesis of Dolastatin 17 will allow further biological studies and assignment of the Doy and Hiv (presumably S configuration as with Dolastatin 15, previously incorporated by reference) absolute configurations. That research is under way and will eventually allow a more detailed assessment of the promising antineoplastic activity.

The administration of Dolastatin 17 is useful for treating neoplastic disease associated with malignant cell growth, and expectedly its synthetic counterpart, as well as, its pharmaceutically and physiologically active derivatives will be useful for treating neoplastic disease associated with malignant cell growth in animals and humans. For example, Dolastatin 17 was screened against a minipanel of the U.S. National Cancer Institute's human cancer cell lines utilizing protocols described by Michael R. Boyd and Kenneth D. Paul in *Some Practical Considerations and Applications of the National Cancer Institute In Vitro Anticancer Drug Discovery Screen*, 34 DRUG DEVELOPMENT RESEARCH 91 (1995) (and references cited therein). Dolastatin 17 was found to display significant human cancer cell growth inhibitory activity against OVCAR-3 (GI$_{50}$ 0.67 μg/ml), SF-295 (GI$_{50}$ 0.55 μg/ml), HCI-H460 (GI$_{50}$ 0.74 μg/ml and KM20L2 (GI$_{50}$ 0.45 μg/ml).

It is expected that unit dosage forms of Dolastatin 17 could be prepared according to selected compositions described in the examples incorporated by reference from U.S. Pat. Nos. 4,414,205, 4,486,414, 4,816,444, 4,879,278, 4,986,988, and 5,138,036 except that Dolastatin 17 would be substituted as the active ingredient (e.g. substitute Dolastatin 17 for Dolastatin 14 in U.S. Pat. No. 5,138,036). Illustratively, expected dosage levels of the administered active ingredients would be: subcutaneously, 1 to about 50 mg/kg; intravenous, 0.4 to about 20 mg/kg; intramuscular, 1 to about 50 mg/kg; orally, 5 to 100 mg/kg; intranasal instillation, 5 to about 100 mg/kg; and aerosol, 5 to 100 mg/kg. As used herein, mg/kg means weight of active ingredients in milligrams divided by the body weight of the host in kilograms. The dose administered will be dependent upon the identity of the neoplastic disease; the type of host involved, including its age, health and weight; the kind of concurrent treatment employed, if any; and the frequency of treatment and therapeutic ratio.

From the foregoing, it becomes readily apparent new and useful antineoplastic preparations have been herein described and illustrated which fulfill all of the aforestated objectives. It is, of course, understood that such modifications, alterations and adaptations as will readily occur to the artisan confronted with this disclosure are intended within the scope of the invention.

4. Structure and Activity of Dolastatin 18

Dolastatin 18 exhibited a FAB-MS quasi-molecular ion peak at m/z 619 ($[M+H]^+$), corresponding to molecular formula $C_{35}H_{46}N_4O_4S$, which was consistent with the carbon and hydrogen content estimated from the NMR spectra as shown in table 3.

TABLE 3

The $^1H$- and $^{13}C$- NMR Spectral Data Assignments of Dolastatin 18 (in $CDCl_3$)

| No. | $^{13}C$ ppm | $^1H$ ppm | J (Hz) | HMBC ($^1H$ to $^{13}C$) |
|---|---|---|---|---|
| 2 | 174.13 s | | | |
| 4 | 139.41 d | 7.50 d | 7.5 | |
| 5 | 119.96 d | 7.38 d | 7.5 | |
| 6 | 52.40 d | 5.63 m | | 2 |
| 6a | 40.87 t | 3.47 dd | 8.0, 19 | 2, 6, 9b, 9c |
| | | 3.37 dd | 7.5, 19 | |
| 6b | 135.80 s | | | |
| 6c | 129.33 d | 7.23 m | | 6a |
| 6d | 128.73 d | 7.26 m | | |
| 6e | 127.23 d | 7.24 m | | |
| 7 | | 7.81 d | 3.5 | |
| 8 | 169.86 s | | | |
| 9 | 57.46 d | 5.10 dd | 6.5, 7.0 | 8, 10 |
| 9a | 33.53 t | 3.30 m | | 9 |
| | | 2.92 m | | 9 |
| 9b | 136.41 s | | | |
| 9c | 128.66 d | 7.28 m | | 9a |
| 9d | 128.50 d | 7.22 m | | |
| 9e | 126.75 d | 7.18 m | | |
| 10 | 31.36 q | 2.89 s | | 9, 11 |
| 11 | 174.04 s | | | |
| 12 | 48.42 d | 4.55 m | | 11, 12a |
| 12a | 41.11 t | 1.05 m | | |
| | | 0.88 m | | |
| 12b | 24.39 d | 1.07 m | | 17 |
| 12c | 21.97 q | 0.73 d | 7.5 | 12a, 12b, 12d |
| 12d | 22.97 q | 0.69 d | 8.0 | 12a, 12b, 12c |
| 13 | | 6.29 d | 8.0 | 14 |
| 14 | 172.80 s | | | |
| 15a | 55.47 s | | | |
| 15b | 22.48 q | 1.30 s | | 14, 15 |
| 15c | 22.55 q | 1.32 s | | 15, 16 |
| 16 | 210.20 s | | | |
| 17 | 40.06 t | 2.42 dt | 4.0, 9.0 | 16, 18, 19 |
| 18 | 17.10 t | 1.52 m | | 16 |
| 19 | 13.59 q | 0.83 t | 8.0 | |

The $^1H$- and $^{13}C$-NMR spectra of Dolastatin 18 exhibited two amide NH, one amide $NCH_3$, and four carbon signals between δ169 and 175 strongly suggesting that Dolastatin 18 is a peptide as shown in table 3, supra. A ketone carbonyl (δ210.60) was also apparent from the NMR spectra. Interpretation of the $^1H$, HCOSY, TOCSY, HMQC and HMBC NMR spectra measured (500 MHZ) in three solvents ($CDCl_3$, $CD_2Cl_2$ and $CD_3CN$), revealed the structure of peptide 4 to be derived from two α-amino acids (Leu and MePhe), dolaphenine (herein named Doe) units and the new carboxylic acid 2,2-dimethyl-3-oxo-hexanoic acid (herein named dolahexanoic acid, Dhex). Interestingly, Dhex appears biosynthetically related to the β-oxo-2,2-dimethyl amino acid unit of Dolastatin 11 (See: G. Pettit, et al., 28 Heterocycles 553 (1989)).

Sequential assignments for the four units were established by the HMBC correlations shown in table 4 with reference to Dolastatin 10 disclosed in U.S. Pat. No. 4,879,278 and previously incorporated by reference. Although no HMBC relationships were observed from the two olefin protons at δ7.38 d (H-4) and δ7.50 d (H-5) to the carbon (C-2) at δ172.2 (s), the coupling constants (J=3.5 Hz) of the proton doublet indicated a cis orientation in a five membered ring. The chemical shifts of the proton and carbon signals led to identification of the thiazole ring. While it proved difficult to find HMBC correlations from NH-7, H-6 and H-8 to C-2 (δ172.2 s), the Doe unit was deduced when it was found the respective NMR data (in $CD_2Cl_2$) nearly coincided with that of Dolastatin 10 (U.S. Pat. No. 4,879,278).

TABLE 4

Comparison of the "Doe" 1 Unit NMR (500 MHZ) Spectral Data from Dolastatin 18 and Dolastatin 10 (in $CD_2Cl_2$).

| Position No. | Dolastatin 18 Doe Unit | | Dolastatin 10 Doe Unit | |
|---|---|---|---|---|
| | Carbon | Proton | Carbon | Proton |
| 2 | 172.20 | | 170.51 | |
| 4 | 146.65 | 7.78 | 147.77 | 7.72 |
| 5 | 119.27 | 7.26 | 118.76 | 7.25 |
| 6 | 53.03 | 5.52 | 53.02 | 5.52 |
| 7 | | 7.28 | | 7.26 |
| 6a | 41.40 | 3.18 | 41.48 | 3.26 |
| | | 3.40 | | 3.40 |

Two important HMBC correlations involving NH—Leu/CO—Dhex and $CH_3N$—Phe/CO—Leu established the Dhex—Leu—MePhe-bonding where Doe and Dhex were assigned the C— and N— terminal position of the sequence, respectively. Although no HMBC correlation was found from NH—Doe to CO—MePhe, the sequence of Dolastatin 18 was deduced to be Dhex—Leu—MePhe—Doe. The structure of Dolastatin 18 elucidated by these NMR and chemical considerations was supported by tandem MS/MS sequential analyses. Thus, the structure elucidated for Dolastatin 18 is (HMBC (⁀) correlations):

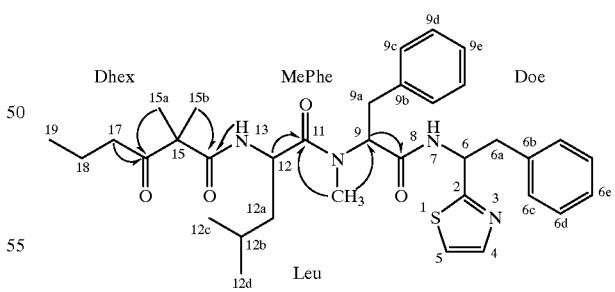

The chiral centers of Leu and MePhe were found to be L and D, respectively, by employing a 6N HCl hydrolysis-chiral HPLC analysis sequence. Conditions for the chiral HPLC analysis included: a 4.6 by 50 mm column containing CHIREX phase 3126 (Phenomenex); two chromatographic solvents: either a 2 mM $CuSO_4$ aqueous solution for α-amino acids and lactic acid, or a 2 mM $H_2O$—$CH_3CN:CuSO_4$ (9:1) solution for 2-hydroxyvaleric acid; and a UV-VIS detection device set at 230.4 nm and 500 nm.

Based on our total synthesis of natural Dolastatin 10 and the x-ray crystal structure determination of 6(R)-Dolastatin 10 the DOE unit of Dolastatin 18 was assigned the 6(S)-configuration.

Assignment of the remaining chiral centers will require a series of synthetic approaches where the overall objective will be a convenient total synthesis. That research is under way and will eventually allow a more detailed assessment of the promising antineoplastic activity.

The administration of Dolastatin 18 is useful for treating neoplastic disease associated with malignant cell growth, and expectedly its synthetic counterpart, as well as, its pharmaceutically and physiologically active derivatives will be useful for treating neoplastic disease associated with malignant cell growth in animals and humans. For example, Dolastatin 18 was screened against a minipanel of the U.S. National Cancer Institute's human cancer cell lines utilizing protocols described by Michael R. Boyd and Kenneth D. Paul in *Some Practical Considerations and Applications of the National Cancer Institute In Vitro Anticancer Drug Discovery Screen*, 34 DRUG DEVELOPMENT RESEARCH 91 (1995) (and references cited therein). Dolastatin 18 was found to significantly inhibit growth of a selection of human cancer cell lines, including lung cancer, where activity against the lung cancer NCI-H460 proved typical at $ED_{50}$ 0.39 μg/mL.

It is expected that unit dosage forms of Dolastatin 18 could be prepared according to selected compositions described in the examples incorporated by reference from U.S. Pat. Nos. 4,414,205, 4,486,414, 4,816,444, 4,879,278, 4,986,988, and 5,138,036 except that Dolastatin 18 would be substituted as the active ingredient (e.g. substitute Dolastatin 18 for Dolastatin 14 in U.S. Pat. No. 5,138,036). Illustratively, expected dosage levels of the administered active ingredients would be: subcutaneously, 1 to about 50 mg/kg; intravenous, 0.4 to about 20 mg/kg; intramuscular, 1 to about 50 mg/kg; orally, 5 to 100 mg/kg; intranasal instillation, 5 to about 100 mg/kg; and aerosol, 5 to 100 mg/kg. As used herein, mg/kg means weight of active ingredients in milligrams divided by the body weight of the host in kilograms. The dose administered will be dependent upon the identity of the neoplastic disease; the type of host involved, including its age, health and weight; the kind of concurrent treatment employed, if any; and the frequency of treatment and therapeutic ratio.

From the foregoing it becomes readily apparent new and useful antineoplastic preparations have been herein described and illustrated which fulfill all of the aforestated objectives. It is of course understood that such modifications, alterations and adaptations as will readily occur to the artisan confronted with this disclosure are intended within the scope of the invention.

What is claimed is:

1. An isolated and purified substance which inhibits neoplastic cell growth denominated Dolastatin 16 and having the following characteristics:

Physical Data for Dolastatin 16
IR (cm$^{-1}$), KBr: 3300, 1600 and 1540;
UV (nm), MeOH: 250, and 240–210;
MS, HRFAB: 871.525713 [M+H]$^+$; and
NMR, 500 MHZ, CLCl$_3$;

The $^1$H and $^{13}$C- MNR Spectral Data Assignments of Dolastatin 16 (in CDCl$_3$)

| No. | $^{13}$C ppm | $^1$H ppm | J (Hz) | HMBC ($^1$H to $^{13}$C) |
|---|---|---|---|---|
| Pro$^1$CO | 172.24 s | | | |
| α | 61.28 d | 4.62 dd | (7.2, 2.0) | CO, β, γ, δ |
| β | 30.70 t | 2.18 m | | |
| | | 2.26 m | | CO, α, γ, |
| γ | 24.78 t | 1.99 m | | |
| | | 2.08 m | | β |
| δ | 47.55 t | 3.45 m | | γ |
| | | 3.91 m | | α, β, γ |
| Dpv$^2$CO | 171.31 s | | | |
| α | 50.59 d | 4.95 d | (7.2) | Pro$^1$CO, CO, β, γ, γ' |
| β | 40.90 d | 1.75 m | | γ |
| γ | 40.95 t | 2.39 m | | α, β, γ, 1, 2/6 |
| | | 2.52 d | (7.6) | α, β, γ, 1, 2/6 |
| γ' | 15.13 q | 0.80 d | (5.2) | α, β, γ |
| 1 | 140.60 s | | | |
| 2/6 | 129.66 d | 7.35 d | (6.0) | γ, 4 |
| 3/4 | 128.33 d | 7.27 d | (6.0) | 1 |
| 5 | 126.15 d | 7.17 d | (6.0, 6.0) | 2/6 |
| NH | | 6.73 d | (7.2) | Pro$^1$CO, CO |
| Pro$^3$CO | 171.01 s | | | |
| α | 58.84 d | 4.55 d | (6.0) | CO, β, γ, δ |
| β | 25.49 t | 1.51 m | | CO |
| γ | 25.01 t | 1.73 m | | α |
| | | 1.84 m | | |
| δ | 45.89 t | 2.52 m | | β |
| | | 2.83 m | | γ |
| Dml$^4$CO | 174.64 s | | | |
| α | 38.67 d | 2.85 m | | CO, β' |
| β | 56.35 d | 3.66 m | | Pro$^3$, CO, CO, α, γ |
| β' | 14.89 q | 1.01 d | (5.6) | CO, α, β |
| γ | 32.31 d | 1.53 m | | |
| δ | 19.73 q | 0.87 d | (5.6) | β, γ, δ' |
| δ' | 20.29 q | 0.88 d | (5.6) | β, γ, δ |
| NH | | 7.68 d | (8.0) | Pro$^3$CO |
| Lac$^5$CO | 169.02 s | | | |
| α | 66.64 d | 5.18 q | (7.0) | Dml$^4$CO, CO, β |
| β | 17.02 q | 1.44 d | (7.0) | CO, α |
| Pro$^6$CO | 171.01 s | | | |
| α | 57.82 d | 4.45 d | (6.4) | CO, β, γ, δ |
| β | 30.82 t | 2.20 m | | CO |
| | | 2.30 m | | CO, δ |
| γ | 21.77 t | 1.95 m | | |
| | | 2.07 m | | β |
| δ | 46.43 t | 3.42 m | | γ |
| | | 3.67 m | | |
| Hiv$^7$CO | 169.57 s | | | |
| α | 76.37 d | 5.42 d | (2.8) | Pro$^6$CO, CO, β, γ, γ' |
| β | 28.29 d | 2.18 m | | γ, γ' |
| γ | 16.08 q | 1.04 d | (7.0) | α, β, γ' |
| γ' | 19.73 q | 1.06 d | (7.2) | α, β, γ |
| MeVal$^8$ | | | | |
| CO | 169.30 s | | | |
| α | 59.46 d | 5.16 | (8.8) | CO, β, γ, γ', CH$_3$N |
| β | 25.63 d | 2.36 m | | α, γ, γ' |
| γ | 19.73 q | 0.91 d | (5.6) | α, β, γ' |
| γ' | 17.75 q | 0.83 d | (5.2) | α, β, γ |
| CH$_3$N | 29.26 q | 3.09 s | | Hiv$^7$CO, CO |

2. An isolated cell growth inhibitory substance according to claim 1 and having the structural formula (HMBC (⌒) and nOe (⌒) correlations):

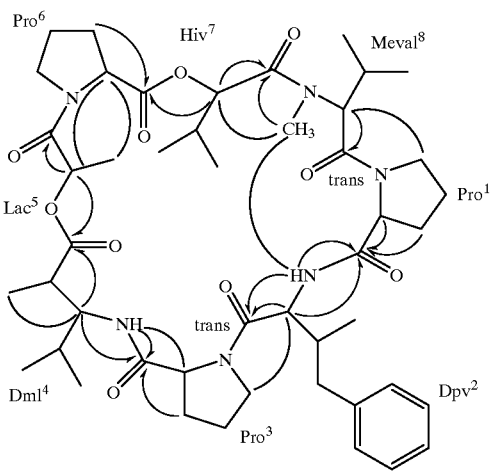

3. An isolated and purified substance which inhibits neoplastic cell growth denominated Dolastatin 17 and having the following characteristics:

Physical Data for Dolastatin 17
IR (cm$^{-1}$), KBr: 3350, 2900, 2116, 1740, 1643, and 1520;
MS, HRFAB: 774.500914 [M+H]$^+$; and
NMR, 500 MHZ, CDCl$_3$;

The $^1$H- and $^{13}$C-NMR Spectral Data Assignments of Dolastatin 17 (in CDCl$_3$)

| No. | $^{13}$C ppm | $^1$H ppm | J (Hz) | HMBC ($^1$H to $^{13}$C) |
|---|---|---|---|---|
| Pro$^1$CO | 171.81 s | | | |
| α | 57.27 d | 5.12 dd | (9.0, 5.0) | CO, β, γ |
| β | 29.68 t | 1.80 m | | CO |
| | | 2.38 m | | CO |
| γ | 24.81 t | 2.00 m | | α, β, δ |
| δ | 47.06 t | 3.55 dd | (9, 7.5) | α, β |
| | | 3.91 m | | α, β |
| MeVal$^2$ | | | | |
| CO | 171.27 s | | | |
| α | 64.51 d | 4.23 d | (8.5) | Pro$^1$CO, CO, β, γ, γ', CH$_3$N |
| β | 29.47 d | 2.35 m | | α, γ, γ' |
| γ | 20.43 q | 1.20 d | (6.5) | α, β, γ' |
| γ' | 21.40 q | 1.07 d | (7.0) | α, β, γ |
| CH$_3$N | 30.49 q | 2.92 s | | Pro$^1$CO, CO, α |
| Hiv$^3$CO | 169.54 | | | |
| α | 76.60 d | 5.21 d | (3.0) | MeVal$^2$CO, CO β, γ, γ' |
| β | 28.92 d | 2.14 m | | γ, γ' |
| γ | 20.07 q | 1.10 d | (7.0) | α, β, γ' |
| γ' | 16.31 q | 0.99 d | (7.0) | α, β, γ |
| MeVal$^4$ | | | | |
| CO | 168.98 s | | | |
| α | 62.15 d | 4.68 d | (10) | Hiv$^3$CO, CO, β, γ, γ' |
| β | 25.58 d | 2.30 m | | α, γ, γ' |
| γ | 17.91 q | 0.78 d | (6.5) | α, β, γ' |
| γ' | 19.83 q | 0.95 d | (7.0) | α, β, γ |
| CH$_3$N | 29.81 q | 2.92 s | | Hiv$^3$CO, CO |
| Lac$^5$CO | 172.08 | | | |
| α | 51.64 d | 4.60 m | | McVal$^4$CO, CO, β, γ |
| β | 38.39 t | 1.68 m | | γ, δ, ι' |
| γ | 24.65 d | 1.61 in | | β, δ, δ' |
| δ | 23.59 q | 0.86 q | (7.0) | β, γ, δ' |
| δ' | 20.87 q | 0.84 q | (7.5) | β, γ, δ |

The $^1$H- and $^{13}$C-NMR Spectral Data Assignments of Dolastatin 17 (in CDCl$_3$)

| No. | $^{13}$C ppm | $^1$H ppm | J (Hz) | HMBC ($^1$H to $^{13}$C) |
|---|---|---|---|---|
| NH | | 7.25 d | (7.8) | McVal$^4$CO, α |
| Doy$^6$CO | 170.17 s | | | |
| α | 39.51 t | 2.27 m | | CO, β, γ |
| | | 2.79 dd | (16.6) | CO, β, γ |
| β | 45.32 d | 4.32 m | | |
| γ | 33.99 t | 1.52 m | | α, β, ε |
| | | 1.64 m | | |
| δ | 24.48 t | 1.52 m | | |
| ε | 18.18 t | 2.16 m | | γ, ζ |
| ζ | 68.43 s | | | |
| ξ | 84.20 d | 1.91 s | | ε |
| NH | | 6.10 d | (7.8) | Leu$^5$CO, α, β |
| Hiv$^7$CO | 167.20 s | | | |
| α | 76.17 d | 5.03 d | (3.0) | Doy$^6$CO, CO, β, γ, γ' |
| β | 29.47 d | 2.35 m | | γ, γ' |
| γ | 16.21 q | 0.98 d | (7.0) | α, β, γ' |
| γ' | 20.02 q | 1.02 d | (7.0) | α, β, γ |

4. An isolated cell growth inhibitory substance according to claim 3 and having the structural formula (HMBC (⌢) and nOe (⌢) correlations):

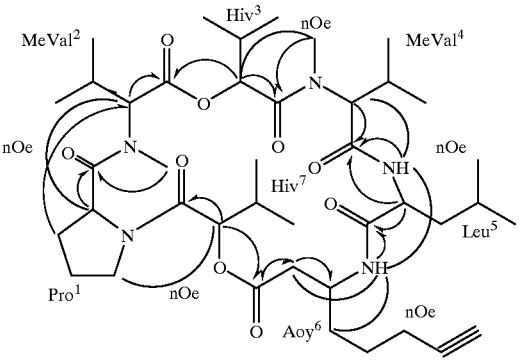

5. An isolated and purified substance which inhibits neoplastic cell growth denominated Dolastatin 18 and having the following characteristics:

Physical Data for Dolastatin 18
MS, HRFAB; 619 [M+H]$^+$; and
NMR, 500 MHZ, CDCl$_3$:

The $^1$H- and $^{13}$C- NMR Spectral Data Assignments of Dolastatin 18 (in CDCl$_3$)

| No. | $^{13}$C ppm | $^1$H ppm | J (Hz) | HMBC ($^1$H to $^{13}$C) |
|---|---|---|---|---|
| 2 | 174.13 s | | | |
| 4 | 139.41 d | 7.50 d | 7.5 | |
| 5 | 119.96 d | 7.38 d | 7.5 | |
| 6 | 52.40 d | 5.63 m | | 2 |
| 6a | 40.87 t | 3.47 dd | 8.0, 19 | 2, 6, 9b, 9c |
| | | 3.37 dd | 7.5, 19 | |
| 6b | 135.80 s | | | |
| 6c | 129.33 d | 7.23 m | | 6a |
| 6d | 128.73 d | 7.26 m | | |
| 6e | 127.23 d | 7.24 m | | |

-continued

The $^1$H- and $^{13}$C- NMR Spectral Data Assignments of Dolastatin 18 (in CDCl$_3$)

| No. | $^{13}$C ppm | $^1$H ppm | J (Hz) | HMBC ($^1$H to $^{13}$C) |
|---|---|---|---|---|
| 7 | | 7.81 d | 3.5 | |
| 8 | 169.86 s | | | |
| 9 | 57.46 d | 5.10 dd | 6.5, 7.0 | 8, 10 |
| 9a | 33.53 t | 3.30 m | | 9 |
| | | 2.92 m | | 9 |
| 9b | 136.41 s | | | |
| 9c | 128.66 d | 7.28 m | | 9a |
| 9d | 128.50 d | 7.22 m | | |
| 9e | 126.75 d | 7.18 m | | |
| 10 | 31.36 q | 2.89 s | | 9, 11 |
| 11 | 174.04 s | | | |
| 12 | 48.42 d | 4.55 m | | 11, 12a |
| 12a | 41.11 t | 1.05 m | | |
| | | 0.88 m | | |
| 12b | 24.39 d | 1.07 m | | 17 |
| 12c | 21.97 q | 0.73 d | 7.5 | 12a, 12b, 12d |
| 12d | 22.97 q | 0.69 d | 8.0 | 12a, 12b, 12c |
| 13 | | 6.29 d | 8.0 | 14 |
| 14 | 172.80 s | | | |
| 15a | 55.47 s | | | |
| 15b | 22.48 q | 1.30 s | | 14, 15 |
| 15c | 22.55 q | 1.32 s | | 15, 16 |
| 16 | 210.20 s | | | |
| 17 | 40.06 t | 2.42 dt | 4.0, 9.0 | 16, 18, 19 |
| 18 | 17.10 t | 1.52 m | | 16 |
| 19 | 13.59 q | 0.83 t | 8.0 | |

6. An isolated cell growth inhibitory substance according to claim 5 and having the structural formula (HMBC ( ⌒ ) correlations):

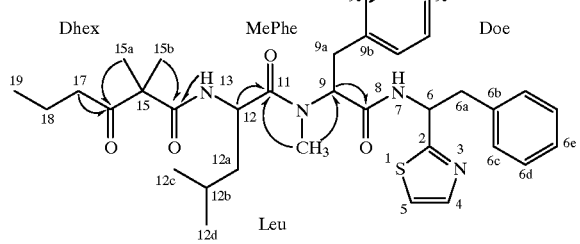

7. A method of inhibiting the growth of neoplastic cells in a host afflicted therewith comprising administering to said host an amount effective to inhibit the growth of said cells of an active ingredient selected from the group consisting of dolastatin 16, dolastatin 17, dolastatin 18 or a pharmaceutically active derivative thereof and a pharmaceutically acceptable carrier.

8. A method according to claim 7 in which active ingredient has the structural formula;

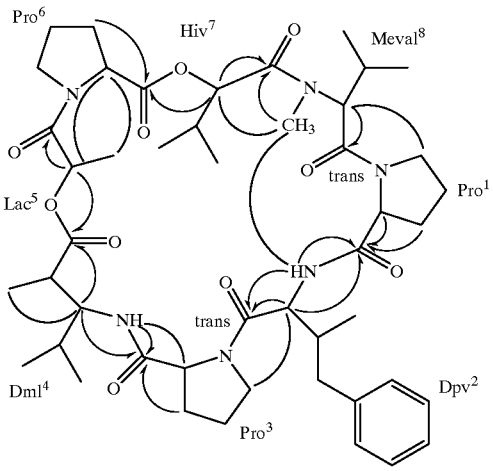

9. A method according to claim 7 in which active ingredient has the structural formula:

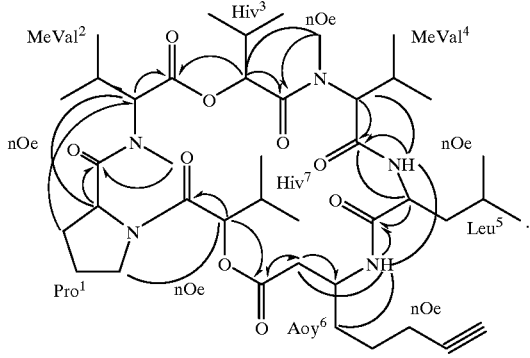

10. A method according to claim 7 in which active ingredient has the structural formula:

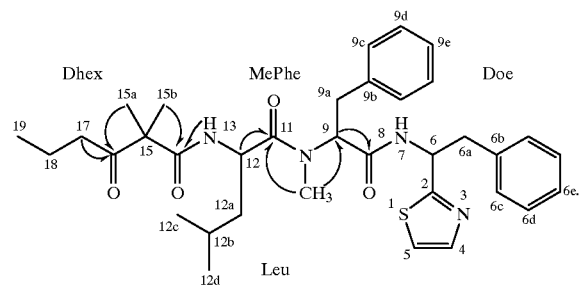

* * * * *